United States Patent [19]

Klausener et al.

[11] Patent Number: 5,231,097
[45] Date of Patent: Jul. 27, 1993

[54] PYRIMIDYL-SUBSTITUTED ACRYLIC ESTERS

[75] Inventors: Alexander Klausener, Krefeld; Peter C. Knüppel, Wermelskirchen; Heinz-Wilhelm Dehne, Monheim; Stefan Dutzmann, Hilden, all of Fed. Rep. of Germany

[73] Assignee: Bayer Aktiengesellschaft, Leverkusen, Fed. Rep. of Germany

[21] Appl. No.: 739,647

[22] Filed: Aug. 2, 1991

[30] Foreign Application Priority Data

Aug. 16, 1990 [DE] Fed. Rep. of Germany ....... 4025891

[51] Int. Cl.$^5$ ............... A61K 31/505; C07D 239/32; C07D 401/04
[52] U.S. Cl. .................................. 514/256; 514/269; 514/274; 544/182; 544/215; 544/238; 544/298; 544/315; 544/316; 544/322; 544/326; 544/330; 544/331; 544/333; 544/335; 544/296
[58] Field of Search ............... 544/298, 322, 326, 330, 544/331, 333, 335, 315, 316, 182, 215, 238, 296; 514/269, 256, 274

[56] References Cited

U.S. PATENT DOCUMENTS

| | | | |
|---|---|---|---|
| 3,553,252 | 1/1971 | Mine et al. | 560/104 |
| 4,652,569 | 3/1987 | Ishikawa et al. | 544/319 |

FOREIGN PATENT DOCUMENTS

| | | |
|---|---|---|
| 0057440 | 8/1982 | European Pat. Off. |
| 0178826 | 4/1986 | European Pat. Off. |
| 0212859 | 3/1987 | European Pat. Off. |

*Primary Examiner*—John M. Ford
*Assistant Examiner*—Y. N. Gupta
*Attorney, Agent, or Firm*—Sprung Horn Kramer & Woods

[57] ABSTRACT

There are described new pyrimidyl-substituted acrylic esters of the general formula (I)

$$\underset{Py-X-C=CH-R^2}{\overset{COOR^1}{|}} \quad (I)$$

in which
Py, X, $R^1$ and $R^2$ have the meaning given in the description, a process for their preparation, and new intermediates.

The compounds of the formula (I) are used as pesticides.

6 Claims, No Drawings

PYRIMIDYL-SUBSTITUTED ACRYLIC ESTERS

The invention relates to new pyrimidyl-substituted acrylic esters, to a process for their preparation, to their use in pesticides, and to intermediates, some of which are new.

It has been disclosed that certain substituted acrylic esters such as, for example, the compound methyl 3-methoxy-2-(2-methylphenyl)-acrylate, have fungicidal properties (cf. for example, EP 178,826). Moreover, it is known that certain pyrimidines such as, for example, the compound 2,4-dichloro-5-methylthiopyrimidinyl 6-thiocyanate, also have fungicidal properties (cf., for example, U.S. Pat. No. 4,652,569; DE-OS (German Published Specification) 3,509,437).

However, the activity of these previously known compounds is not entirely satisfactory in all fields of application, in particular when low application rates and concentrations are used.

New pyrimidyl-substituted acrylic esters of the general formula (I)

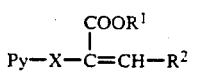  (I)

in which
R$^1$ represents alkyl,
R$^2$ represents dialkylamino or a radical —O—R$^3$,
X represents oxygen, sulphur or a radical

and
Py represents optionally substituted pyrimidyl, where
R$^3$ represents alkyl or optionally substituted aralkyl
and
R$^4$ represents hydrogen, alkyl or in each case optionally substituted aralkyl or aryl, have been found.

The compounds of the formula (I) can exist as geometric isomers or mixtures of isomers of various compositions. The invention claims the pure isomers as well as the mixtures of isomers.

Furthermore, it has been found that the new pyrimidyl-substituted acrylic esters of the general formula (I)

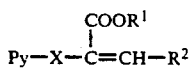  (I)

in which
R$^1$ represents alkyl,
R$^2$ represents dialkylamino or a radical —O—R$^3$,
X represents oxygen, sulphur or a radical

and
Py represents optionally substituted pyrimidyl, where
R$^3$ represents alkyl or optionally substituted aralkyl
and
R$^4$ represents hydrogen, alkyl or in each case optionally substituted aralkyl or aryl, and their isomers or mixtures of isomers are obtained when substituted acetic esters of the formula (II)

in which
R$^1$, Py and X have the abovementioned meaning are reacted with alkoxy-bis-(dialkylamino)-methane compounds of the formula (III)

in which
R$^{2-1}$ represents dialkylamino and
R$^5$ represents alkyl or cycloalkyl, if appropriate in the presence of a diluent and, if appropriate, the resulting 3-dialkylaminoacrylic acid derivatives of the formula (Ia)

in which
R$^1$, R$^{2-1}$, Py and X have the abovementioned meaning, are, in a 2nd step, subsequently hydrolysed with dilute mineral acids and the resulting 3-hydroxyacrylic esters of the formula (IV)

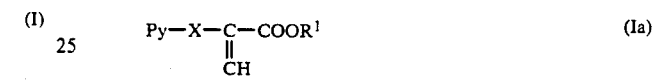

in which
R$^1$, X and Py have the abovementioned meaning, are, in a 3rd step, subsequently reacted with alkylating agents of the formula (V)

$$R^3-E^1 \qquad (V)$$

in which
E$^1$ represents an electron-attracting leaving group and
R$^3$ has the abovementioned meaning, if appropriate in the presence of a diluent and if appropriate in the presence of a reaction auxiliary.

Finally, it has been found that the new pyrimidyl-substituted acrylic esters of the general formula (I) have a good action against pests.

Surprisingly, the pyrimidyl-substituted acrylic esters of the general formula (I) according to the invention show a considerably better fungicidal activity than the acrylic esters known from the prior art such as, for example, the compound methyl 3-methoxy-2-(2-methylphenyl)-acrylate or the compound 2,4-dichloro-5-methylthiopyrimidinyl 6-thiocyanate, which are similar compounds chemically and from the point of view of their action.

Formula (I) provides a general definition of the pyrimidyl-substituted acrylic esters according to the invention. Preferred compounds of the formula (I) are those in which R[1] represents a straight-chain or branched alkyl having 1 to 6 carbon atoms, R[2] represents dialkylamino having in each case 1 to 6 carbon atoms in the individual alkyl moieties, or represents a radical —O—R[3], X represents oxygen, sulphur or a radical $$-\underset{R^4}{N}-$$

and

Py represents 2-pyrimidyl, 4-pyrimidyl or 5-pyrimidyl, each of which is monosubstituted or polysubstituted by identical or different substituents, suitable substituents in each case being: halogen, cyano, nitro, in each case straight-chain or branched alkyl, alkoxy or alkylthio, each of which has 1 to 9 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl, alkoximinoalkyl, dialkylamino or dialkylaminocarbonyl, each of which has 1 to 4 carbon atoms in the individual alkyl moieties, in each case straight-chain or branched alkenyl or alkinyl, each of which has 2 to 8 carbon atoms, cycloalkyl or cycloalkenyl, each of which has 3 to 7 carbon atoms and each of which is optionally monosubstituted or polysubstituted by $C_1$-$C_4$-alkyl, or double-linked alkanediyl having 3 to 5 carbon atoms, or aryl, aryloxy, arylthio, arylamino, N-alkylarylamino, arylcarbonyl, aralkyl, arylalkenyl, arylalkinyl, arylalkyloxy, arylalkylthio, heteroaryl, heteroaryloxy, heteroarylthio, heteroarylamino, N-alkylheteroarylamino, heteroarylcarbonyl, heteroarylalkyl, heteroarylalkenyl, heteroarylalkinyl, heteroarylalkyloxy or heteroarylalkylthio, each of which has 6 to 10 carbon atoms in the aryl moiety or 2 to 9 carbon atoms and 1 to 4 identical or different heteroatoms—in particular nitrogen, oxygen and/or sulphur—in the heteroaryl moiety and, if appropriate, 1 to 6 carbon atoms in the straight-chain or branched alkyl moiety or, if appropriate, 2 to 6 carbon atoms in the straight-chain or branched alkenyl or alkinyl moiety, and each of which is optionally monosubstituted or polysubstituted in the aryl moiety or heteroaryl moiety by identical or different substituents from the series comprising halogen, alkyl, cycloalkyl, alkoxy, alkylthio, halogenoalkyl, halogenoalkoxy, halogenoalkylthio, formyl, dioxyalkylene, halogen-substituted dioxyalkylene, or in each case optionally substituted phenyl, phenoxy, benzyl, phenylethyl, phenylethenyl or phenylethinyl; where R[3] represents a straight-chain or branched alkyl having 1 to 6 carbon atoms or aralkyl having 1 to 4 carbon atoms in the straight-chain or branched alkyl moiety and 6 to 10 carbon atoms in the aryl moiety, and R[4] represents hydrogen, straight-chain or branched alkyl having 1 to 6 carbon atoms, or represents aralkyl or aryl with 1 to 6 carbon atoms in the straight-chain or branched alkyl moiety and 6 to 10 carbon atoms in the particular aryl moiety, each of which is optionally monosubstituted or polysubstituted in the aryl moiety by identical or different substituents, suitable substituents in the aryl moiety in each case being those mentioned in the case of Py.

Particularly preferred compounds of the formula (I) are those in which

R[1] represents methyl, ethyl, n- or i-propyl, or n-, i-, s- or t-butyl,

R[2] represents dialkylamino having in each case 1 to 4 carbon atoms in the individual alkyl moieties, or represents a radical —O—R[3], X represents oxygen, sulphur or a radical $$-\underset{R^4}{N}-$$

and

Py represents 2-pyrimidyl or 4-pyrimidyl, each of which is monosubstituted to trisubstituted by identical or different substituents, where at least one substituent represents phenyl, naphthyl, phenoxy, phenylthio, N-methyl-phenylamino, phenylcarbonyl, benzyl, phenylethyl, phenylpropyl, phenylethenyl, phenylethinyl, benzyloxy, cyclohexenyl or heteroaryl, each of which is optionally monosubstituted to trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy, formyl, trifluoromethylthio, dioxymethylene, dioxyethylene, tetrafluorodioxyethylene, difluorodioxymethylene, cyclopentyl, cyclohexyl, or comprising phenyl, phenoxy, benzyl, phenylethyl, phenylethenyl or phenylethinyl, each of which is optionally monosubstituted to trisubstituted by identical or different substituents [by fluorine, chlorine, methyl, methoxy or trifluoromethyl]- and suitable individual heteroaryl radicals being those which follow:

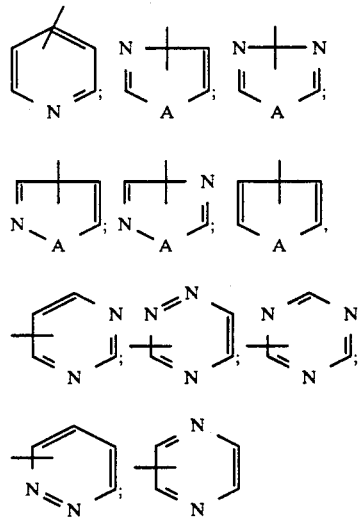

which can also optionally be benzo-fused and in which

A in each case represents oxygen, sulphur or an NH group;

in addition, the following other pyrimidyl substituents are preferably suitable: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trichloromethoxy, trifluoromethylthio, methoxycarbonyl, ethoxycarbonyl, methoximinomethyl, ethoximinomethyl, methoximinoethyl, ethoximinoethyl, dimethylamino, diethylamino, dimethylcarbamoyl, diethylcarbamoyl, allyl, butenyl, ethinyl, vinyl, propargyl, cyclopentyl, cyclohexyl, 1,3-propanediyl or 1,4-butanediyl; where R³ represents methyl, ethyl, n- or i-propyl, n-, i-, s- or t-butyl or benzyl and R⁴ represents hydrogen, methyl, ethyl, n- or i-propyl, n-, i-, s- or t-butyl, or benzyl or phenyl.

Very particularly preferred compounds of the formula (I) are those in which

R¹ represents methyl or ethyl,

R² represents methoxy or ethoxy,

X represents a radical

and

Py represents 2-pyrimidyl or 4-pyrimidyl, each of which is monosubstituted to trisubstituted by identical or different substituents, where at least one substituent in each case represents phenyl, naphthyl, phenoxy, cyclohexenyl, cyclohexyl, benzyl, pyridyl, pyrimidyl, pyrazolyl, oxazolyl, thiazolyl, thienyl, furyl, thiadiazolyl, oxadiazolyl, imidazolyl or triazolyl, each of which is optionally benzo-fused and/or monosubstituted to trisubstituted by identical or different substituents from the series comprising fluorine, chlorine, bromine, methyl, ethyl, t-butyl, methoxy, ethoxy, trifluoromethyl, trifluoromethoxy, dioxymethylene, difluorodioxymethylene dioxyethylene, tetrafluorodioxyethylene, phenylethenyl, phenylethinyl, benzyl, cyclohexyl, phenoxy, methoxyphenyl, formyl or phenyl, and the following are suitable in each case as additional pyrimidyl substituents: fluorine, chlorine, bromine, cyano, nitro, methyl, ethyl, methoxy, ethoxy, methylthio, trifluoromethyl, trichloromethyl, trifluoromethoxy, trifluoromethylthio, methoxycarbonyl, ethoxycarbonyl dimethylamino, cyclopentyl, cyclohexyl, 1,3-propanediyl or 1,4-butanediyl, and where R⁴ represents methyl, ethyl or benzyl.

Aryl as such or in compositions represents phenyl or naphthyl, in particular phenyl.

All aliphatic radicals as such or in compositions are straight-chain or branched.

Unless otherwise defined, halogen represents fluorine, chlorine, bromine or iodine, in particular fluorine, chlorine or bromine.

The following pyrimidyl-substituted acrylic esters of the general formula (I) may be mentioned individually in addition to the compounds mentioned in the preparation examples:

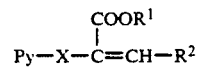

| Py | R¹ | R² | X |
|---|---|---|---|
| 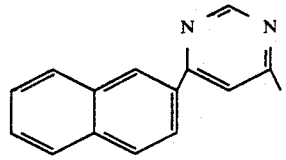 | CH₃ | OCH₃ | —N—<br>\|<br>CH₃ |

-continued

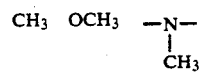

| Py | R¹ | R² | X |
|---|---|---|---|
| 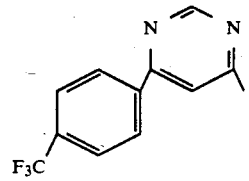 | CH₃ | OCH₃ | —N—<br>\|<br>CH₃ |
| 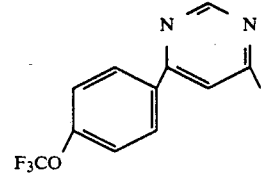 | CH₃ | OCH₃ | —N—<br>\|<br>CH₃ |
| 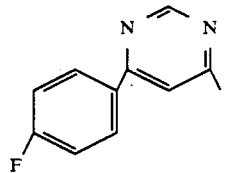 | CH₃ | OCH₃ | —N—<br>\|<br>CH₃ |
| 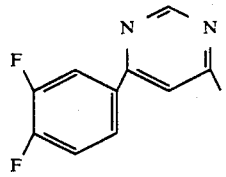 | CH₃ | OCH₃ | —N—<br>\|<br>CH₃ |
| 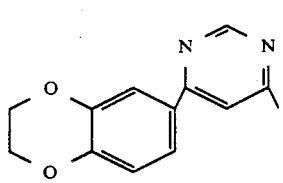 | CH₃ | OCH₃ | —N—<br>\|<br>CH₃ |
| 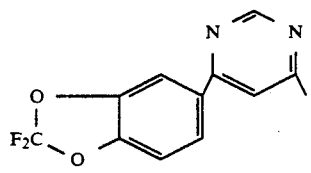 | CH₃ | OCH₃ | —N—<br>\|<br>CH₃ |
| 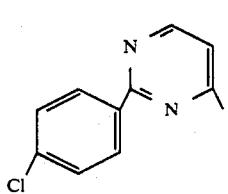 | CH₃ | OCH₃ | —N—<br>\|<br>CH₃ |

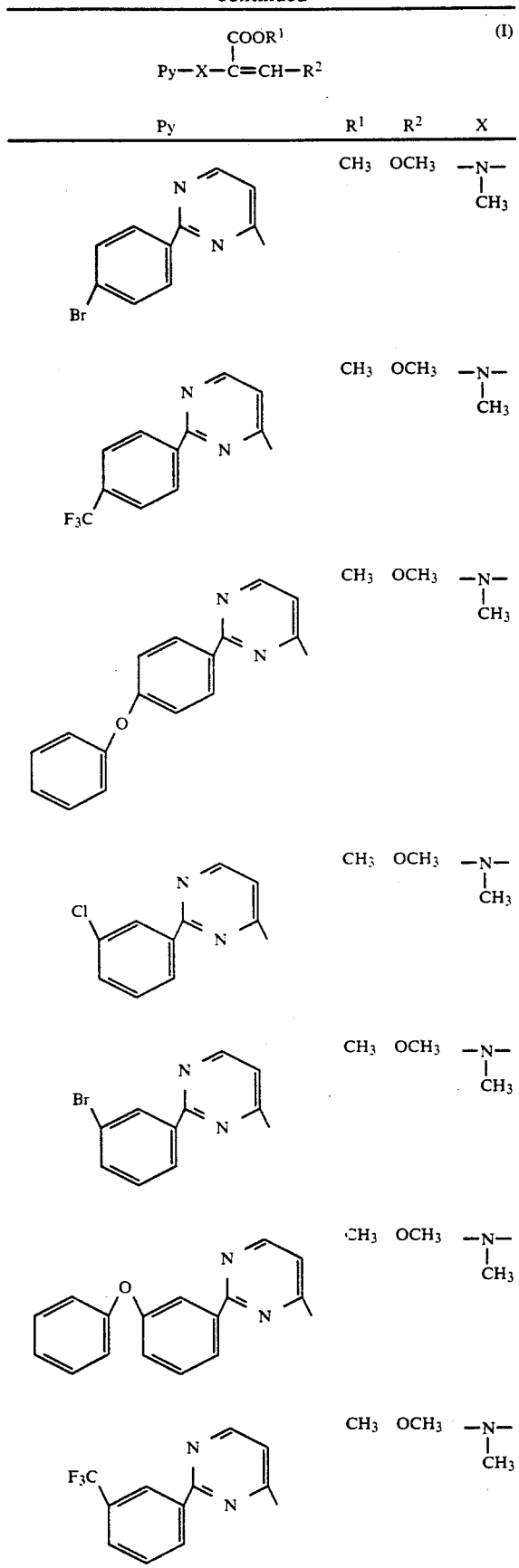
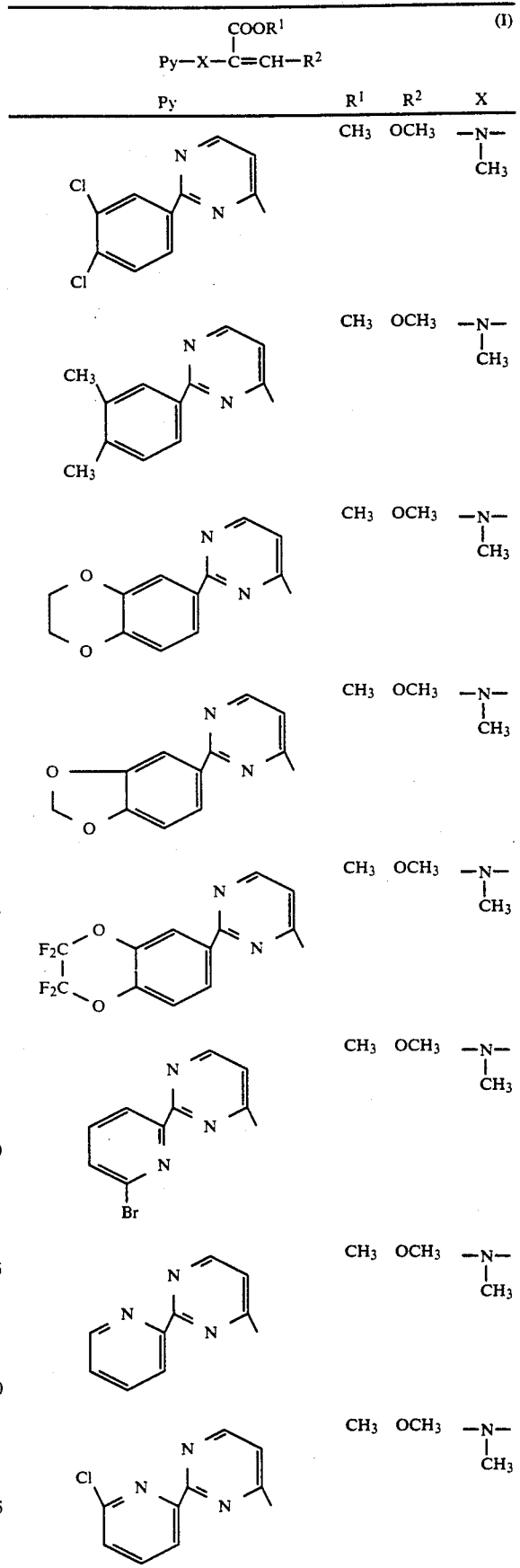

-continued $$Py-X-\underset{\underset{CH=CH-R^2}{|}}{\overset{COOR^1}{C}} \quad (I)$$

| Py | R¹ | R² | X |
|---|---|---|---|
| 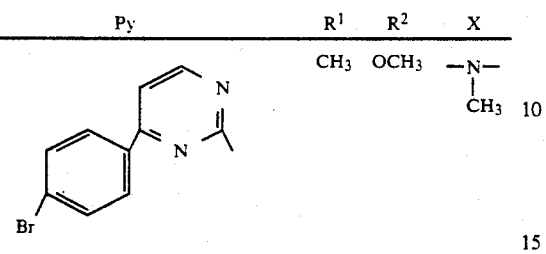 (4-Br-phenyl) | CH₃ | OCH₃ | —N(CH₃)— |
| 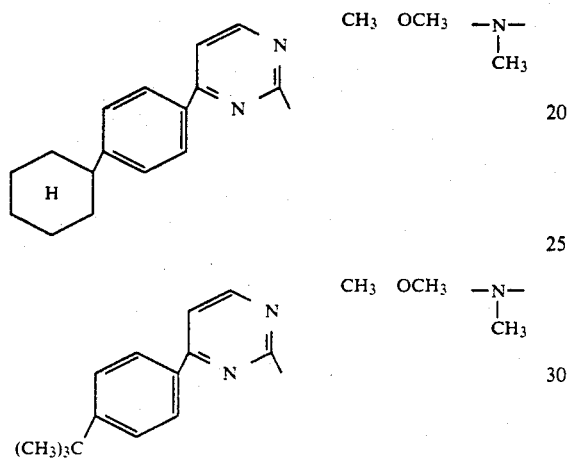 (4-cyclohexyl-phenyl) | CH₃ | OCH₃ | —N(CH₃)— |
| (CH₃)₃C-phenyl | CH₃ | OCH₃ | —N(CH₃)— |
| F₃CO-phenyl | CH₃ | OCH₃ | —N(CH₃)— |
| 3-CH₃-phenyl | CH₃ | OCH₃ | —N(CH₃)— |
| 3-Br-phenyl | CH₃ | OCH₃ | —N(CH₃)— |
| 3-phenoxy-phenyl | CH₃ | OCH₃ | —N(CH₃)— |

-continued $$Py-X-\underset{\underset{CH=CH-R^2}{|}}{\overset{COOR^1}{C}} \quad (I)$$

| Py | R¹ | R² | X |
|---|---|---|---|
| 3,4-difluoro-phenyl | CH₃ | OCH₃ | —N(CH₃)— |
| 3,4-methylenedioxy-phenyl | CH₃ | OCH₃ | —N(CH₃)— |
| 3-OCH₃-4-Cl-phenyl | CH₃ | OCH₃ | —N(CH₃)— |
| 2-naphthyl | CH₃ | OCH₃ | —N(CH₃)— |
| 3-methyl-cyclohexenyl | CH₃ | OCH₃ | —N(CH₃)— |
| 2-thienyl | CH₃ | OCH₃ | —N(CH₃)— |
| 5-chloro-2-thienyl | CH₃ | OCH₃ | —N(CH₃)— |

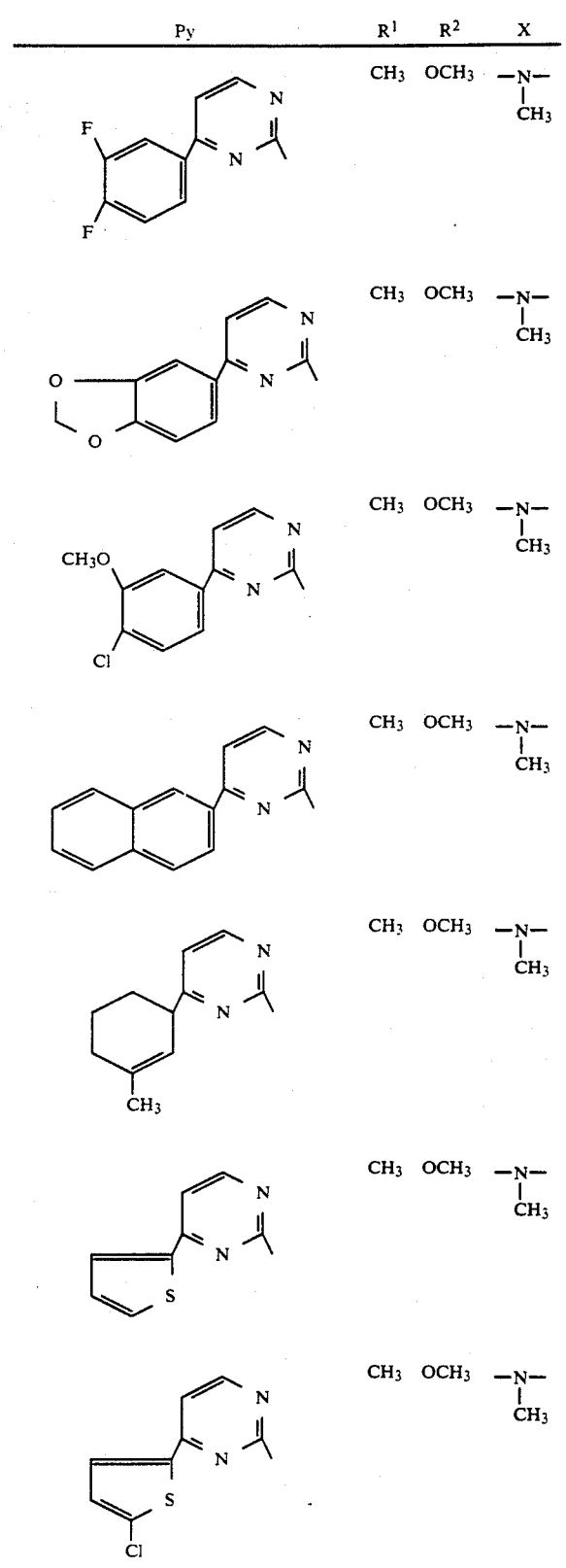

-continued $$Py-X-\underset{COOR^1}{\underset{|}{C}}=CH-R^2 \quad (I)$$

| Py | R¹ | R² | X |
|---|---|---|---|
| 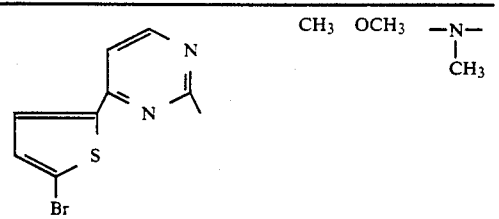 | CH₃ | OCH₃ | —N—CH₃ |
| 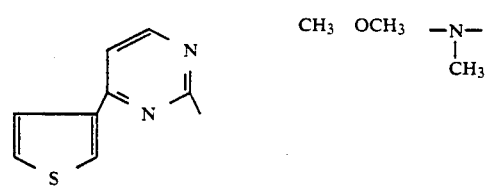 | CH₃ | OCH₃ | —N—CH₃ |
| 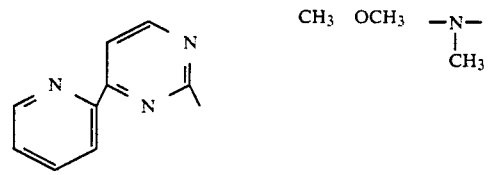 | CH₃ | OCH₃ | —N—CH₃ |
| 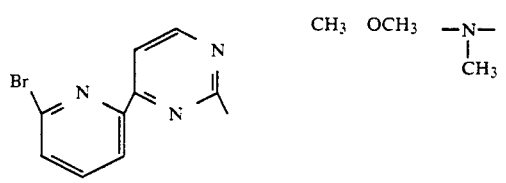 | CH₃ | OCH₃ | —N—CH₃ |
| 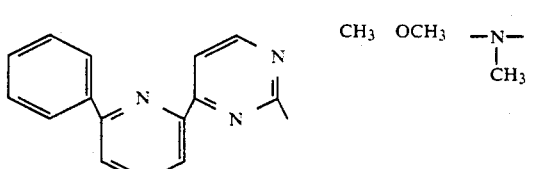 | CH₃ | OCH₃ | —N—CH₃ |
| 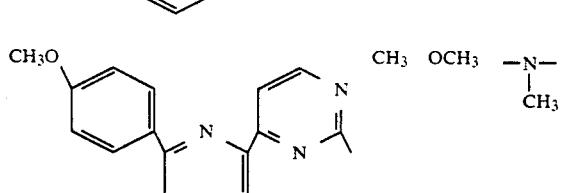 | CH₃ | OCH₃ | —N—CH₃ |
| 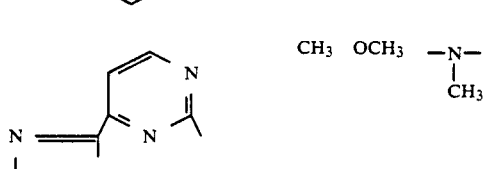 | CH₃ | OCH₃ | —N—CH₃ |
| 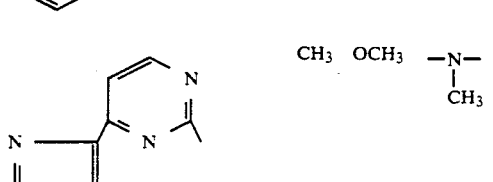 | CH₃ | OCH₃ | —N—CH₃ |

-continued $$Py-X-\underset{COOR^1}{\underset{|}{C}}=CH-R^2 \quad (I)$$

| Py | R¹ | R² | X |
|---|---|---|---|
| 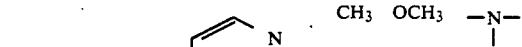 | CH₃ | OCH₃ | —N—CH₃ |
|  | CH₃ | OCH₃ | —N—CH₃ |
|  | CH₃ | OCH₃ | —N—CH₃ |
|  | CH₃ | OCH₃ | —N—CH₃ |
|  | CH₃ | OCH₃ | —N—CH₃ |
|  | CH₃ | OCH₃ | —N—CH₃ |
|  | CH₃ | OCH₃ | —N—CH₃ |

If, for example, methyl N-[4-(6-phenyl)-pyrimidinyl]-N-methylaminoacetate and t-butoxybis(dimethylamino)-methane as well as dimethyl sulphate are used as starting substances, the course of the reaction of the process according to the invention can be outlined by the following equation:

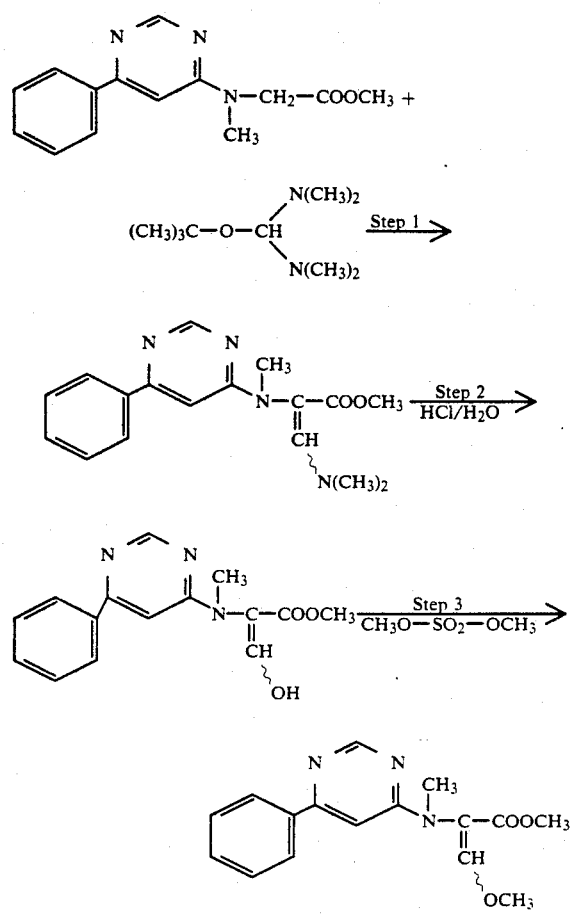

Formula (II) provides a general definition of the substituted acetic esters required as starting substances for carrying out the process according to the invention.

In this formula (II), $R^1$, Py and X preferably represent those radicals which have already been mentioned in connection with the description of the substances of the formula (I) according to the invention as being preferred for these substituents.

The substituted acetic esters of the formula (II) are known in some cases (cf., for example, Liebigs Ann. Chem. 1988, 633–642; Anal. Chem. 58, 1681–1685 [1986]; JP 58,198,472; ZA 7,308,543; DE-OS (German Published Specification) 2,342,881) or can be obtained in analogy to known processes (cf., for example, Chem. Pharm. Bull. 32. 497–503 [1984]; EP 326,389; Austral. J. Chem. 32, 669–679 [1979]; EP 310,550; J. Heterocycl. Chem. 18, 183–184 [1981]; J. Heterocycl. Chem. 19, 1165 [1982]; DE-OS (German Published Specification) 3,807,532; Rev. Trav. Chim. Pays-Bas 86, 15–25 [1967]; J. Amer. Chem. Soc. 90, 5518 et seq. [1968]).

Formula (III) provides a general definition of the alkoxy-bis-(dialkylamino)-methane compounds furthermore required as starting substances for carrying out the process according to the invention. In this formula (III), $R^{2-1}$ preferably represents dialkylamino having in each case 1 to 6 carbon atoms, particularly preferably 1 to 4 carbon atoms, in the individual straight-chain or branched alkyl moieties.

$R^5$ preferably represents secondary or tertiary alkyl having 3 to 8 carbon atoms, or cycloalkyl having 5 to 7 carbon atoms, in particular t-butyl or cyclohexyl.

The alkoxy-bis(dialkylamino)-methane derivatives of the formula III are also known (cf., for example, Chem. Ber, 101, 41–50 [1968]; Chem. Ber. 101, 1885–1888 [1968]; DE 2,303,919; PCT Int. Appl. WO 8601204) or can be obtained in analogy to known processes.

The intermediates of the formula IV are new and also a subject of the invention.

Formula (V) provides a general definition of the alkylating agents furthermore required as starting substances for carrying out step 3 of the process according to the invention. In this formula (V), $R^3$ preferably represents those radicals which have already been mentioned in connection with the description of the substances of the formula (I) according to the invention, as being preferred for this substituent.

$E^1$ represents a leaving group customary in the case of alkylating agents, preferably an optionally substituted alkyl, alkoxy or arylsulphonyloxy radical such as, for example, a methoxysulphonyloxy radical, an ethoxysulphonyloxy radical or a p-toluenesulphonyloxy radical, or represents halogen, in particular chlorine, bromine or iodine.

The alkylating agents of the formula (V) are generally known compounds of organic chemistry.

Suitable diluents for carrying out the 1st step of the process according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, amides such as dimethylformamide, dimethylacetamide, N-methylformanilide, N-methylpyrrolidone or hexamethylphosphoric triamide.

It is also possible to carry out the 1st step of the process according to the invention entirely without the addition of solvents.

When carrying out the 1st step of the process according to the invention, the reaction temperatures can be varied within a substantial range. In general, the process is carried out at temperatures between $-35°$ C. and $+150°$ C., preferably at temperatures between $0°$ C. and $120°$ C.

The 1st step of the process according to the invention can also be carried out under reduced or increased pressure, but is preferably carried out under atmospheric pressure.

If appropriate, the use of an inert gas atmosphere such as, for example, nitrogen or argon, can be expedient, but it is generally possible to carry out the 1st step of the process according to the invention in an ordinary room atmosphere.

For carrying out the 1st step of the process according to the invention, 1.0 to 15.0 mols, preferably 1.0 to 5.0 mols, of alkoxy-bis-(dialkylamino)-methane compound of the formula (III) are generally employed per mole of substituted acetic ester of the formula (II).

The reaction is carried out and the reaction products are worked up and isolated by generally customary methods (cf. also the Preparation Examples).

Suitable acids for carrying out hydrolysis in the 2nd step of the process according to the invention are customary inorganic and organic acids. Aqueous solutions of inorganic mineral acids such as hydrochloric acid, sulphuric acid, phosphoric acid or nitric acid; in particular aqueous hydrochloric acid, are preferably used.

Suitable diluents for carrying out the 2nd and 3rd step of the process according to the invention are also inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide.

The 2nd step of the process according to the invention is carried out, in particular, in polar diluents such as acetonitrile, acetone or dimethylformamide, if appropriate also in the presence of water.

If desired, the 3rd step of the process according to the invention can also be carried out in a two-phase system such as, for example, water/toluene or water/dichloromethane, if appropriate in the presence of a phase-transfer catalyst. The following may be mentioned as examples of such catalysts: tetrabutylammonium iodide, tetrabutylammonium bromide, tributylmethylphosphonium bromide, trimethyl-$C_{13}/C_{15}$-alkylammonium chloride, dibenzyldimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

The 3rd step of the process according to the invention is preferably carried out in the presence of a suitable reaction auxiliary. Suitable reaction auxiliaries are all inorganic and organic bases which can customarily be used. The following are preferably used: the hydrides, hydroxides, amides, alcoholates, carbonates or hydrogen carbonates of alkali metal such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the 2nd and 3rd steps of the process according to the invention, the reaction temperatures can be varied within a substantial range. In general, the process is carried out at temperatures between $-30°$ C. and $+150°$ C., preferably at temperatures between $-20°$ C. and $+120°$ C.

Both the 2nd step of the process according to the invention and the 3rd step of the process according to the invention are generally carried out under atmospheric pressure. However, it is also possible to carry out these steps under reduced or increased pressure.

For carrying out the 2nd step of the process according to the invention, 1.0 to 3.0 mols, preferably 1.0 to 2.0 mols, of dilute mineral acid are generally employed per mole of 3-dialkylaminoacrylic ester of the formula (Ia). The reaction is carried out and the reaction products are worked up and isolated by generally customary methods.

For carrying out the 3rd step of the process according to the invention, 1.0 to 5.0 mols, preferably 1.0 to 3.0 mols, of alkylating agent of the formula (V) and, if appropriate, 1.0 to 5.0 mols, preferably 1.0 to 3.0 mols, of reaction auxiliary are generally employed per mole of 3-hydroxyacrylic ester of the formula (IV). The reaction is carried out and the reaction products are worked up and isolated by generally customary methods.

In a particularly preferred variant, the 2nd and the 3rd reaction step of the process according to the invention are carried out in a so-called "one-pot reaction" directly in one reaction step, without isolation of the intermediates of the formula (IV). In this variant too, the reaction is carried out and the reaction products are worked up and isolated by generally customary methods (cf. also the preparation examples).

The active substances according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe spcies, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the pathogen causing powdery mildew on wheat or barley (*Erysiphe graminis*) or against the pathogen causing barley leaf spot (*Cochliobolus sativus*) or against the pathogen causing snow mould of cereals (*Fusarium nivale*) or against the pathogen causing glume blotch of wheat (*Leptosphaeria nodorum*) or against the pathogen causing net blotch on barley (*Pyrenophora teres*) or for combating rice diseases, such as, for example, against the pathogen causing rice blast disease (*Pyricularia oryzae*) or against the pathogen causing rice stem blight (*Pellicularia sasakii*) or for combating diseases in fruit and vegetable growing such as, for example, against the pathogen causing tomato blight (*Phytophthora infectans*) or against the pathogen causing downy mildew on grape vine (*Plasmopara viticola*). The good in-vitro activity of the active compounds according to the invention must also be emphasised. The intermediates of the formulae (II) and (IV) are also fungicidally active.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol, polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture of with-/other known active compounds such as fungicides, insecticides, acaricides and herbicides, as well as mixtures with fertilizers and growth regulators.

The active compounds can be used as such, in the form of their formulations or the use forms prepared therefrom such as ready-to-use solutions, suspensions, wettable powders, pastes, soluble powders, dusts and granules. They are applied in a customary manner, for example by pouring, spraying, atomising, scattering, dusting, foaming, brushing on and the like. It is furthermore possible to apply the active compounds by the ultra-low-volume method or to inject the active compound preparation or the active compound itself into the soil. The seed of the plants can also be treated.

In the treatment of parts of plants, the active compound concentrations in the use forms can be varied within a substantial range. They are generally between 1 and 0.0001% by weight, preferably between 0.5 and 0.001%.

In the treatment of seeds, amounts of active compound of 0.001 to 50 g per kilogram of seed, preferably 0.01 to 10 g, are generally required.

In the treatment of the soil, active compound concentrations of 0.00001 to 0.1% by weight, preferably 0.0001 to 0.02%, are required at the site of action.

PREPARATION EXAMPLES

Example 1

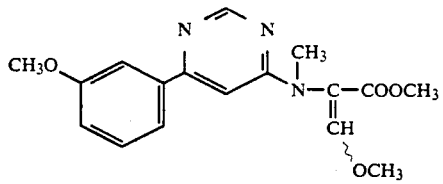

To 6 g (0.017 mol) of methyl 2-{N-[6-(3-methoxyphenyl)-pyrimidin-4-yl]-N-methylamino}-3-dimethylaminoacrylate in 600 ml of acetone there are first added 600 ml of water and subsequently 18 ml (0.035 mol) 2-normal hydrochloric acid, and the mixture is subsequently stirred for 8 hours at room temperature. After this, acetone is distilled off, and the aqueous solution is rendered neutral and extracted using ethyl acetate. The organic phase is concentrated, the residue is taken up in 100 ml of dimethylformamide, the mixture is treated with 4.8 g (0.035 mol) of potassium carbonate and 4.4 g (0.035 mol) of dimethyl sulphate and stirred for 16 hours at room temperature. For working up, the mixture is concentrated in vacuo, and the residue is partitioned between ethyl acetate and water. The organic phase is concentrated and the residue chromatographed on silica gel (eluent: ethyl acetate).

2.8 g (50% of theory) of methyl 2-{N-[6-(3-methoxyphenyl)-pyrimidin-4-yl]-N-methylamino}-3-methoxyacrylate of melting point 87°–90° C. are obtained.

Example 2

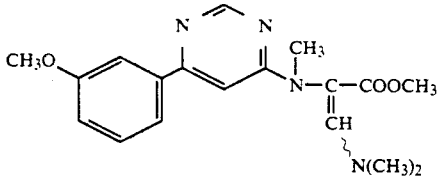

To 15 g (0.052 mol) of methyl N-[6-(3-methoxyphenyl)-4-pyrimidinyl]-N-methylglycinate there are added 54.6 g (0.313 mol) of t-butyloxy-bis-(dimethylamino)methane. After the reaction mixture has been stirred for 16 hours at 80° C., it is poured into water and extracted with ethyl acetate. The combined dried ethyl acetate phases are concentrated.

15.9 g (89% of Theory) of methyl 2-{N-[6-(3-methoxyphenyl)pyrimidin-4-yl]-N-methylamino}-3-dimethylaminoacrylate of melting point 172°–174° C. are obtained.

PREPARATION OF THE STARTING COMPOUND

Example II-1

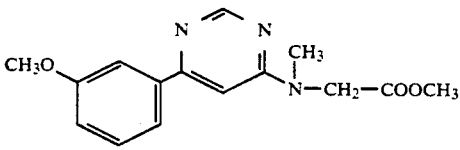

To 47.6 g (0.216 mol) of 4-chloro-6-(3-methoxyphenyl)pyrimidine in 600 ml of dioxane there are added 60.2 g (0.431 mol) of methyl sarcosinate hydrochloride and 65.5 g (0.647 mol) of triethylamine, and this reaction mixture is heated at reflux temperature for 16 hours. Another 12.4 g (0.089 mol) of methyl sarcosinate hydrochloride and 13.0 g (0.128 mol) of triethylamine are then added and the mixture is heated at reflux temperature for another 6 hours. For working up, the mixture is treated with water and extracted using ethyl acetate. The combined dried ethyl acetate phases are concentrated in vacuo.

50.6 g (82% of theory) of methyl N-[(3-methoxyphenyl-4-pyrimidyl)-N-methyl]-glycinate of melting point 50°–52° C. are obtained.

Example 3

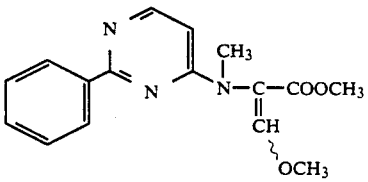

To 10 g (0.032 mol) of methyl 2-[N-(2-phenylpyrimidin-4-yl)-N-methylamino]-3-dimethylaminoacrylate in 100 ml of dimethylformamide there are added 33 ml (0.064 mol) 2-normal hydrochloric acid, the reaction mixture is stirred for 4 hours at 50° C. and then poured into water, and this mixture is rendered neutral and extracted using ethyl acetate. The ethyl acetate phase is concentrated, the residue is dissolved in 100 ml of dimethylformamide, the solution is treated with 13.3 g (0.096 mol) of potassium carbonate and 4.5 g (0.035 mol) of dimethyl sulphate, and stirred for 5 hours at room temperature. For working up, the reaction mixture is poured into water, extracted with ethyl acetate, the organic phase is concentrated, and the residue is crystallized by stirring with diisopropyl ether.

5.9 g (62% of theory) of methyl 3-methoxy-2-[N-(2-phenylpyrimidin-4-yl)-N-methylamino]-acrylate of melting point 152°–154° C. are obtained.

Example 4

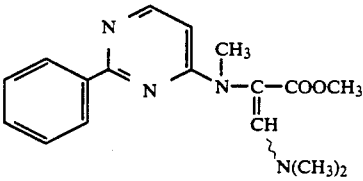

To 19.0 g (0.074 mol) of methyl N-(2-phenyl-4-pyrimidyl)-N-methylglycinate there are added 51.6 g (0.295 mol) of t-butyloxy-bis-(dimethylamino)methane. After the reaction mixture has been stirred for 16 hours at 100° C., it is poured into water and extracted with ethyl acetate. The combined dried ethyl ester phases are concentrated.

23.0 g (100% of theory) of methyl 2-[N-(2-phenylpyrimidin-4-yl)-N-methylamino]-3-dimethylaminoacrylate are obtained as an oil.

$^1$H NMR (CDCl$_3$ tetramethylsilane): δ=2.91 ppm (6H) N(CH$_3$)$_2$; 3.62 ppm (3H) COOCH$_3$; 3.34 ppm (3H) N-CH$_3$

PREPARATION OF THE STARTING COMPOUND

Example II-2

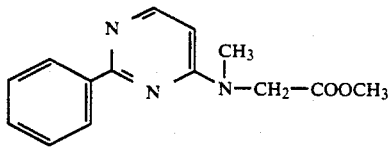

To 17.7 g (0.093 mol) of 4-chloro-2-phenyl-pyrimidin in 250 ml of dioxane there are added 19.5 g (0.139 mol) of methyl sarcosinate hydrochloride and 28.2 g (0.279 mol) of triethylamine, this reaction mixture is heated for 20 hours at 100° C. For working up, the reaction mixture is treated with water and extracted using ethyl acetate. The combined dried ethyl acetate phases are concentrated in vacuo.

21.9 g (92% of theory) of 4-chloro-6-(3-methoxyphenyl)pyrimidine of melting point 112°–115° C. are obtained.

Example 5

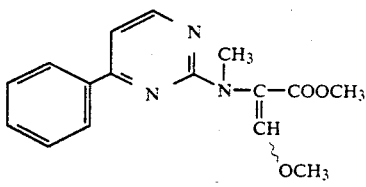

To 10 g (0.032 mol) of methyl 2-[N-(4-phenylpyrimidin-2-yl)-N-methylamino]-3-dimethylaminoacrylate in 80 ml of dimethylformamide there are added 33.5 ml (0.064 mol) of 2-normal hydrochloric acid, the reaction mixture is stirred for 4 hours at 50° C. and then poured into water, rendered neutral and extracted using ethyl acetate. The ethyl acetate phase is concentrated, the residue is dissolved in 80 ml of dimethylformamide, the solution is treated with 13.3 g (0.096 mol) of potassium carbonate and 4.5 g (0.035 mol) of dimethyl sulphate and stirred for 16 hours at room temperature. For working up, the reaction mixture is poured into water and extracted using ethyl acetate, the organic phase is concentrated, and the residue is stirred with diisopropyl ether, filtered off with suction and dried.

7.5 g (78% of Theory) of methyl 3-methoxy-2-[N-(4-phenylpyrimidin-2-yl)-N-methylamino]-acrylate of melting point 123°–125° C. are obtained.

Example 6

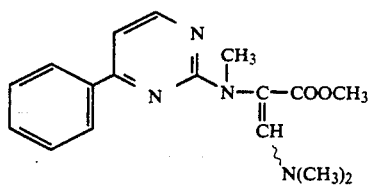

To 23.9 g (0.093 mol) of methyl N-(4-phenyl-2-pyrimidyl)-N-methylglycinate there are added 64.6 g (0.372 mol) of t-butyloxy-bis-(dimethylamino)methane. After the reaction mixture has been stirred for 20 hours at 100° C., it is poured into water and extracted using ethyl acetate. The combined, dried ethyl acetate phases are concentrated in vacuo.

27.0 g (93% of Theory) of methyl 2-[N-(4-phenyl-pyrimidin-2-yl)-N-methylamino]-3-dimethylaminoacrylate of melting point 101° C. are obtained.

PREPARATION OF THE STARTING COMPOUND

Example II-3

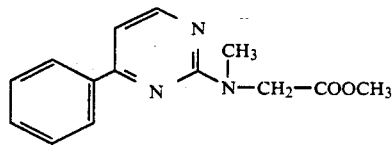

To 46.5 g (0.294 mol) of 2-chloro-4-phenyl-pyrimidin in 500 ml of dioxane there are added 51.1 g (0.366 mol) of methyl sarcosinate hydrochloride and 74.0 g (0.732 mol) of triethylamine, and this reaction mixture is heated for 16 hours at 100° C. For working up, the reaction mixture is treated with water and extracted using ethyl acetate. The combined dried ethyl acetate phases are concentrated in vacuo.

60.9 g (97% of theory) of methyl N-(4-phenyl-2-pyrimidyl)-N-methyl glycinate are obtained as an oil.

$^1$H NMR (CDCl$_3$ tetramethylsilane): δ=3.35 ppm (3H) N-CH$_3$; 4.45 ppm (2H) —CH$_2$—; 3.74 ppm (3H) —COOCH$_3$.

The following pyrimidyl-substituted acrylic esters of the general formula (I)

$$Py-X-C(COOR^1)=CH-R^2 \quad (I)$$

are obtained in a corresponding manner and following the general preparation instructions:

| Example No. | Py | R$^1$ | R$^2$ | X | Physical properties |
|---|---|---|---|---|---|
| 7 | 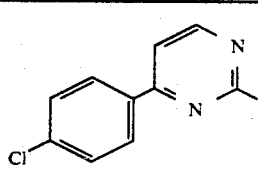 | CH$_3$ | —N(CH$_3$)$_2$ | —N(CH$_3$)— | Mp.: 111° C. |

-continued

The following pyrimidyl-substituted acrylic esters of the general formula (I)

$$Py-X-\underset{\underset{COOR^1}{|}}{C}=CH-R^2 \qquad (I)$$

are obtained in a corresponding manner and following the general preparation instructions:

| Example No. | Py | R¹ | R² | X | Physical properties |
|---|---|---|---|---|---|
| 8 | 4-Cl-phenyl-pyrimidine | CH₃ | —OCH₃ | —N(CH₃)— | Mp.: 108–109° C. |
| 9 | 4-CH₃O-phenyl-pyrimidine | CH₃ | —N(CH₃)₂ | —N(CH₃)— | Mp.: 157–160° C. |
| 10 | 4-F-phenyl-pyrimidine | CH₃ | —N(CH₃)₂ | —N(CH₃)— | ¹H NMR*): 3.64; 2.96; 3.35 |
| 11 | 4-CH₃O-phenyl-pyrimidine | CH₃ | —OCH₃ | —N(CH₃)— | Mp.: 80–83° C. |
| 12 | 4-biphenyl-pyrimidine | CH₃ | —N(CH₃)₂ | —N(CH₃)— | Mp.: 214–216° C. |
| 13 | 4-Cl-phenyl-pyrimidine | CH₃ | —N(CH₃)₂ | —N(CH₃)— | Mp.: 169–171° C. |
| 14 | 3,4-diCl-phenyl-pyrimidine | CH₃ | —N(CH₃)₂ | —N(CH₃)— | Mp.: 148–150° C. |
| 15 | 3,4-diCH₃-phenyl-pyrimidine | CH₃ | —N(CH₃)₂ | —N(CH₃)— | Mp.: 140–142° C. |

-continued

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 16 | (4-Cl-phenyl)-pyrimidine | CH₃ | —OCH₃ | —N(CH₃)— | Mp.: 145° C. |
| 17 | (3,4-diCl-phenyl)-pyrimidine | CH₃ | —OCH₃ | —N(CH₃)— | Mp.: 148° C. |
| 18 | (3,4-diCH₃-phenyl)-pyrimidine | CH₃ | —OCH₃ | —N(CH₃)— | Mp.: 120–123° C. |
| 19 | 2-methyl-4-(4-F-phenyl)-pyrimidine | CH₃ | —OCH₃ | —N(CH₃)— | Mp.: 97–99° C. |
| 20 | 2-methyl-4-(3,4-diOCH₃-phenyl)-pyrimidine | CH₃ | —N(CH₃)₂ | —N(CH₃)— | ¹H NMR*): 3.65; 2.96; 3.36 |
| 21 | 2-methyl-4-(3-CF₃-phenyl)-pyrimidine | CH₃ | —N(CH₃)₂ | —N(CH₃)— | ¹H NMR*): 3.65; 3.36; 2.97 |
| 22 | 2-methyl-4-(3,4-diCH₃-phenyl)-pyrimidine | CH₃ | —N(CH₃)₂ | —N(CH₃)— | ¹H NMR*): 3.64; 3.35; 2.95 |
| 23 | 2-methyl-4-(2-phenyl-thiazolyl)-pyrimidine | CH₃ | —N(CH₃)₂ | —N(CH₃)— | Mp.: 166–168° C. |

-continued

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 24 | 4-(4-cyclohexylphenyl)pyrimidin-6-yl | CH₃ | —N(CH₃)₂ | —N(CH₃)— | Mp.: 141–142° C. |
| 25 | 4-(3-methoxyphenyl)pyrimidin-6-yl | CH₃ | —N(CH₃)₂ | —N(CH₃)— | ¹H NMR*): 3.64; 3.35; 2.95 |
| 26 | 4-(4-methylphenyl)pyrimidin-6-yl | CH₃ | —N(CH₃)₂ | —N(CH₃)— | ¹H NMR*): 3.64; 3.34; 2.95 |
| 27 | 4-(3-trifluoromethylphenyl)pyrimidin-6-yl | CH₃ | —OCH₃ | —N(CH₃)— | Mp.: 83–84° C. |
| 28 | 4-(3,4-dimethylphenyl)pyrimidin-6-yl | CH₃ | —OCH₃ | —N(CH₃)— | Mp.: 122° C. |
| 29 | 4-(4-bromophenyl)pyrimidin-6-yl | CH₃ | —N(CH₃)₂ | —N(CH₃)— | Mp.: 183–186° C. |
| 30 | 4-(4-methylphenyl)pyrimidin-6-yl | CH₃ | —N(CH₃)₂ | —N(CH₃)— | Mp.: 137–140° C. |
| 31 | 4-(3-bromophenyl)pyrimidin-6-yl | CH₃ | —N(CH₃)₂ | —N(CH₃)— | Mp.: 165–168° C. |

The following pyrimidyl-substituted acrylic esters of the general formula (I)

$$Py-X-\underset{\|}{\underset{C}{C}}=CH-R^2 \quad\quad (I)$$
$$\overset{COOR^1}{|}$$

are obtained in a corresponding manner and following the general preparation instructions:

| Example No. | Py | R¹ | R² | X | Physical properties |
|---|---|---|---|---|---|
| 32 | 3-Cl-phenyl-pyrimidin-4-yl | CH₃ | —N(CH₃)₂ | —N(CH₃)— | Mp.: 138–142° C. |
| 33 | 3-CH₃-phenyl-pyrimidin-4-yl | CH₃ | —N(CH₃)₂ | —N(CH₃)— | Mp.: 164–168° C. |
| 34 | 3-F₃C-phenyl-pyrimidin-4-yl | CH₃ | —N(CH₃)₂ | —N(CH₃)— | Mp.: 123–125° C. |
| 35 | 3-CH₃-phenyl-pyrimidin-4-yl | CH₃ | —N(CH₃)₂ | —N(CH₃)— | Mp.: 118–119° C. |
| 36 | 4-phenyl-phenyl-pyrimidin-4-yl | CH₃ | —N(CH₃)₂ | —N(CH₃)— | Mp.: 194–196° C. |
| 37 | 4-(phenylethynyl)phenyl-pyrimidin-4-yl | CH₃ | —N(CH₃)₂ | —N(CH₃)— | Mp.: 138–140° C. |
| 38 | 3-phenyl-phenyl-pyrimidin-4-yl | CH₃ | —N(CH₃)₂ | —N(CH₃)— | ¹H NMR*): 3.66; 3.28; 2.95 |

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 39 | pyrimidine with 3-(phenylethynyl)phenyl substituent | $CH_3$ | $-N(CH_3)_2$ | $-N(CH_3)-$ | Mp.: 141–144° C. |
| 40 | pyrimidine with 3-chloro-4-methoxyphenyl substituent | $CH_3$ | $-N(CH_3)_2$ | $-N(CH_3)-$ | Mp.: 112–113° C. |
| 41 | 2-methyl-pyrimidine with 4-phenoxyphenyl substituent | $CH_3$ | $-N(CH_3)_2$ | $-N(CH_3)-$ | Mp.: 104–105° C. |
| 42 | 2-methyl-pyrimidine with 3,4-dichlorophenyl substituent | $CH_3$ | $-N(CH_3)_2$ | $-N(CH_3)-$ | ¹H NMR*): 3.56; 3.26; 2.88 |
| 43 | 2-methyl-pyrimidine with 5-chlorothien-2-yl substituent | $CH_3$ | $-N(CH_3)_2$ | $-N(CH_3)-$ | Mp.: 113–115° C. |
| 44 | 2-methyl-pyrimidine with biphenyl substituent | $CH_3$ | $-OCH_3$ | $-N(CH_3)-$ | Mp.: 195–196° C. |
| 45 | pyrimidine with 4-bromophenyl substituent | $CH_3$ | $-OCH_3$ | $-N(CH_3)-$ | Mp.: 157–161° C. |

-continued

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 46 | 3-Br-phenyl-pyrimidin-4-yl | $CH_3$ | $-OCH_3$ | $-N(CH_3)-$ | Mp.: 136–139° C. |
| 47 | 3-Cl-phenyl-pyrimidin-4-yl | $CH_3$ | $-OCH_3$ | $-N(CH_3)-$ | Mp.: 127–130° C. |
| 48 | 3-phenyl-phenyl-pyrimidin-4-yl | $CH_3$ | $-OCH_3$ | $-N(CH_3)-$ | Mp.: 148° C. |
| 49 | 3-CH₃-phenyl-pyrimidin-4-yl | $CH_3$ | $-OCH_3$ | $-N(CH_3)-$ | Mp.: 117–120° C. |
| 50 | 4-CH₃-phenyl-pyrimidin-4-yl | $CH_3$ | $-OCH_3$ | $-N(CH_3)-$ | Mp.: 126–129° C. |
| 51 | 3-CF₃-phenyl-pyrimidin-4-yl | $CH_3$ | $-OCH_3$ | $-N(CH_3)-$ | Mp.: 105–108° C. |
| 52 | 3,4-dimethoxy-phenyl-pyrimidin-4-yl | $CH_3$ | $-OCH_3$ | $-N(CH_3)-$ | Mp.: 108–110° C. |
| 53 | 3,4-dimethoxy-phenyl-pyrimidin-4-yl | $CH_3$ | $-N(CH_3)_2$ | $-N(CH_3)-$ | ¹H NMR*): 3.66; 3.26; 2.95 |

-continued

The following pyrimidyl-substituted acrylic esters of the general formula (I)

$$Py-X-\underset{\underset{COOR^1}{|}}{C}=CH-R^2 \qquad (I)$$

are obtained in a corresponding manner and following the general preparation instructions:

| Example No. | Py | R¹ | R² | X | Physical properties |
|---|---|---|---|---|---|
| 54 | 4-(3,4-methylenedioxyphenyl)-6-methylpyrimidin-5-yl | CH₃ | —N(CH₃)₂ | —N(CH₃)— | Mp.: 154–157° C. |
| 55 | 4-(3-chloro-4-methoxyphenyl)-6-methylpyrimidin-5-yl | CH₃ | —N(CH₃)₂ | —N(CH₃)— | Mp.: 176–179° C. |
| 56 | 4-(3-methoxyphenyl)-2-methylpyrimidin-5-yl | CH₃ | —OCH₃ | —N(CH₃)— | ¹H NMR*): 3.67; 3.40; 3.88 |
| 57 | 4-(4-methoxyphenyl)-2-methylpyrimidin-5-yl | CH₃ | —OCH₃ | —N(CH₃)— | ¹H NMR*): 3.70; 3.39; 3.88 |
| 58 | 4-(3-chloro-4-methoxyphenyl)-2-methylpyrimidin-5-yl | CH₃ | —OCH₃ | —N(CH₃)— | ¹H NMR*): 3.71; 3.39; 3.89 |
| 59 | 4-(3,4-dichlorophenyl)-2-methylpyrimidin-5-yl | CH₃ | —OCH₃ | —N(CH₃)— | ¹H NMR*): 3.72; 3.38; 3.90 |
| 60 | 4-(3,4-dimethoxyphenyl)-6-methylpyrimidin-5-yl | CH₃ | —OCH₃ | —N(CH₃)— | Mp. 132–135° C. |
| 61 | 4-(4-tert-butylphenyl)-2-methylpyrimidin-5-yl | CH₃ | —N(CH₃)₂ | —N(CH₃)— | ¹H NMR*): 3.64; 3.35; 2.94 |

-continued

The following pyrimidyl-substituted acrylic esters of the general formula (I)

are obtained in a corresponding manner and following the general preparation instructions:

| Example No. | Py | $R^1$ | $R^2$ | X | Physical properties |
|---|---|---|---|---|---|
| 62 | 2-methyl-4-(thiophen-2-yl)pyrimidin-6-yl | $CH_3$ | $-N(CH_3)_2$ | $-N(CH_3)-$ | $^1$H NMR*): 3.63; 3.30; 2.94 |
| 63 | 2-methyl-4-(3-phenoxyphenyl)pyrimidin-6-yl | $CH_3$ | $-N(CH_3)_2$ | $-N(CH_3)-$ | $^1$H NMR*): 3.56; 3.18; 2.85 |
| 64 | 2-methyl-4-(3,4-methylenedioxyphenyl)pyrimidin-6-yl | $CH_3$ | $-OCH_3$ | $-N(CH_3)-$ | Mp.: 107–111° C. |
| 65 | 2-methyl-4-(3-chloro-4-methoxyphenyl)pyrimidin-6-yl | $CH_3$ | $-OCH_3$ | $-N(CH_3)-$ | $^1$H NMR*): 3.75; 3.27; 3.93 |
| 66 | 2-methyl-4-(biphenyl-4-yl)pyrimidin-6-yl | $CH_3$ | $-OCH_3$ | $-N(CH_3)-$ | Mp.: 142–145° C. |
| 67 | 2-methyl-4-(4-phenoxyphenyl)pyrimidin-6-yl | $CH_3$ | $-N(CH_3)_2$ | $-N(CH_3)-$ | $^1$H NMR*): 3.65; 3.27; 2.94 |
| 68 | 2-methyl-4-(4-chloro-3-methoxyphenyl)pyrimidin-6-yl | $CH_3$ | $-N(CH_3)_2$ | $-N(CH_3)-$ | $^1$H NMR*): 3.66; 3.27; 2.95 |

-continued

The following pyrimidyl-substituted acrylic esters of the general formula (I)

$$Py-X-\underset{\underset{\displaystyle CH-R^2}{\|}}{\underset{\displaystyle C}{C}}\text{OOR}^1 \quad (I)$$

are obtained in a corresponding manner and following the general preparation instructions:

| Example No. | Py | R¹ | R² | X | Physical properties |
|---|---|---|---|---|---|
| 69 | (structure) | CH₃ | —OCH₃ | —N(CH₃)— | Mp.: 129–132° C. |
| 70 | (structure) | CH₃ | —OCH₃ | —N(CH₃)— | Mp.: 124–127° C. |
| 71 | (structure) | CH₃ | —OCH₃ | —N(CH₃)— | Mp.: 136–138° C. |
| 72 | (structure) | CH₃ | —OCH₃ | —N(CH₃)— | Mp.: 102–105° C. |
| 73 | (structure) | CH₃ | —OCH₃ | —N(CH₃)— | ¹H NMR*): 3.73; 3.27; 3.89 |
| 74 | (structure) | CH₃ | —OCH₃ | —N(CH₃)— | Mp.: 118–121° C. |
| 75 | (structure) | CH₃ | —OCH₃ | —N(CH₃)— | ¹H NMR*): 3.71; 3.38; 3.88 |

-continued

The following pyrimidyl-substituted acrylic esters of the general formula (I)

are obtained in a corresponding manner and following the general preparation instructions:

| Example No. | Py | $R^1$ | $R^2$ | X | Physical properties |
|---|---|---|---|---|---|
| 76 | (5-chloro-thienyl-pyrimidinyl structure) | CH$_3$ | —OCH$_3$ | —N(CH$_3$)— | Mp.: 123–124° C. |
| 77 | (4-cyclohexyl-phenyl-pyrimidinyl structure) | CH$_3$ | —OCH$_3$ | —N(CH$_3$)— | Mp.: 114–115° C. |
| 78 | (4-methoxyphenyl-thiazolyl-pyrimidinyl with CHO) | CH$_3$ | —OCH$_3$ | —N(CH$_3$)— | Mp.: 188–189° C. |
| 79 | (benzodioxolyl-pyrimidinyl structure) | CH$_3$ | —N(CH$_3$)$_2$ | —N(CH$_3$)— | Mp.: 104–109° C. |
| 80 | (pyridyl-pyrimidinyl structure) | CH$_3$ | —N(CH$_3$)$_2$ | —N(CH$_3$)— | $^1$H NMR*): 3.64; 3.36; 2.95 |
| 81 | (4-tert-butylphenyl-pyrimidinyl structure) | CH$_3$ | —OCH$_3$ | —N(CH$_3$)— | Mp.: 125–133° C. |
| 82 | (thienyl-pyrimidinyl structure) | CH$_3$ | —OCH$_3$ | —N(CH$_3$)— | Mp.: 115–116° C. |

-continued

The following pyrimidyl-substituted acrylic esters of the general formula (I)

$$Py-X-\underset{\underset{COOR^1}{|}}{C}=CH-R^2 \quad (I)$$

are obtained in a corresponding manner and following the general preparation instructions:

| Example No. | Py | R¹ | R² | X | Physical properties |
|---|---|---|---|---|---|
| 83 | (structure) | CH₃ | —OCH₃ | —N(CH₃)— | Mp.: 156–158° C. |
| 84 | (structure) | CH₃ | —N(CH₃)₂ | —N(CH₃)— | Mp.: 165–168° C. |
| 85 | (structure) | CH₃ | —OCH₃ | S | Mp.: 80–81° C. |
| 86 | (structure) | CH₃ | —OCH₃ | S | Mp.: 120°C. |
| 87 | (structure) | CH₃ | —OCH₃ | —N(CH₃)— | ¹H NMR*): 3.74; 3.30; 3.91 |
| 88 | (structure) | CH₃ | —OCH₃ | S | Mp.: 118°C. |
| 89 | (structure) | CH₃ | —OCH₃ | —N(CH₃)— | Mp.: 106–111° C. |

-continued

The following pyrimidyl-substituted acrylic esters of the general formula (I)

$$Py-X-\underset{\underset{C=CH-R^2}{|}}{\overset{COOR^1}{|}}$$  (I)

are obtained in a corresponding manner and following the general preparation instructions:

| Example No. | Py | R¹ | R² | X | Physical properties |
|---|---|---|---|---|---|
| 90 | 4,6-dimethyl-2-phenylpyrimidin-5-yl | CH₃ | —OCH₃ | —N(CH₃)— | ¹H NMR*): 3.74; 3.35; 3.90 |
| 91 | 4-methyl-6-trifluoromethyl-2-phenylpyrimidin-5-yl | CH₃ | —OCH₃ | —N(CH₃)— | ¹H NMR*): 3.76; 3.40; 3.93 |
| 92 | 2-isopropyl-4-[2-(phenylethynyl)thien-3-yl]pyrimidin-5-yl | CH₃ | —OCH₃ | —N(CH₃)— | |
| 93 | 2-methyl-4-(3-phenoxyphenyl)pyrimidin-5-yl | CH₃ | —OCH₃ | —N(CH₃)— | Mp.: 85–87° C. |
| 94 | 2-methyl-4-(5-bromothien-2-yl)pyrimidin-5-yl | CH₃ | —OCH₃ | —N(CH₃)— | Mp.: 121–122° C. |
| 95 | 2-methyl-4-(5-bromothien-2-yl)pyrimidin-5-yl | CH₃ | —N(CH₃)₂ | —N(CH₃)— | Mp.: 121–123° C. |

-continued

The following pyrimidyl-substituted acrylic esters of the general formula (I)

are obtained in a corresponding manner and following the general preparation instructions:

| Example No. | Py | $R^1$ | $R^2$ | X | Physical properties |
|---|---|---|---|---|---|
| 96 | 2-methyl-4-(3-phenoxyphenyl)pyrimidine | $CH_3$ | $-N(CH_3)_2$ | $-N(CH_3)-$ | Mp.: 110–117° C. |
| 97 | 2-methyl-4-(4-trifluoromethoxyphenyl)pyrimidine | $CH_3$ | $-OCH_3$ | $-N(CH_3)-$ | |
| 98 | 2-methyl-4-(4-methylcyclohex-3-enyl)pyrimidine | $CH_3$ | $-OCH_3$ | $-N(CH_3)-$ | |
| 99 | 2-methyl-4-(thien-3-yl)pyrimidine | $CH_3$ | $-OCH_3$ | $-N(CH_3)-$ | Mp.: 123° C. |
| 100 | 2-methyl-4-(4'-methoxybiphenyl-4-yl)pyrimidine | $CH_3$ | $-OCH_3$ | $-N(CH_3)-$ | Mp.: 161–162° C. |

-continued

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 101 | pyrimidine-4-yl-(4-OCF₃-phenyl) | CH₃ | —N(CH₃)₂ | —N(CH₃)— | |
| 102 | pyrimidine-4-yl-(3-(phenylethynyl)phenyl) | CH₃ | —OCH₃ | —N(CH₃)— | |
| 103 | pyrimidine-4-yl-(3-phenyl-phenyl) | CH₃ | —OCH₃ | —N(CH₃)— | |
| 104 | pyrimidine-4-yl-(4'-OCH₃-biphenyl-4-yl) | CH₃ | —N(CH₃)₃ | —N(CH₃)— | Mp.: 173–175° C. |
| 105 | pyrimidine-4-yl-(4'-OCH₃-biphenyl-3-yl) | CH₃ | —OCH₃ | —N(CH₃)— | |

-continued

The following pyrimidyl-substituted acrylic esters of the general formula (I)

$$Py-X-\underset{\underset{CH=CH-R^2}{|}}{C}OOR^1 \qquad (I)$$

are obtained in a corresponding manner and following the general preparation instructions:

| Example No. | Py | R¹ | R² | X | Physical properties |
|---|---|---|---|---|---|
| 106 | (2-methylpyrimidin-4-yl)–C₆H₄–C≡C–C₆H₅ | CH₃ | —OCH₃ | —N(CH₃)— | Mp.: 142–143° C. |
| 107 | (2-methylpyrimidin-4-yl)–(3-phenylphenyl) | CH₃ | —N(CH₃)₃ | —N(CH₃)— | |
| 108 | (2-methylpyrimidin-4-yl)–C₆H₄–C≡C–C₆H₅ | CH₃ | —N(CH₃)₂ | —N(CH₃)— | Mp.: 75–76° C. |
| 109 | (2-methylpyrimidin-4-yl)–(3-(4-methoxyphenyl)phenyl) | CH₃ | —N(CH₃)₃ | —N(CH₃)— | Mp.: 160–161° C. |

-continued

The following pyrimidyl-substituted acrylic esters of the general formula (I)

$$Py-X-\underset{\underset{COOR^1}{|}}{C}=CH-R^2 \quad (I)$$

are obtained in a corresponding manner and following the general preparation instructions:

| Example No. | Py | $R^1$ | $R^2$ | X | Physical properties |
|---|---|---|---|---|---|
| 110 | pyrimidin-4-yl—C₆H₄—C≡C—C₆H₅ | CH₃ | —N(CH₃)₂ | —N(CH₃)— | Mp.: 209–210° C. |
| 111 | pyrimidin-4-yl—naphthyl | CH₃ | —OCH₃ | —N(CH₃)— | Mp.: 127–129° C. |
| 112 | pyrimidin-4-yl—C₆H₄—Br (para) | CH₃ | —OCH₃ | —N(CH₃)— | Mp.: 94–95° C. |
| 113 | pyrimidin-4-yl—C₆H₄—Br (meta) | CH₃ | —OCH₃ | —N(CH₃)— | |
| 114 | pyrimidin-4-yl—C₆H₃(Cl)(OCH₃) | CH₃ | —OCH₃ | —N(CH₃)— | |

-continued

The following pyrimidyl-substituted acrylic esters of the general formula (I) 

$$Py-X-\underset{\underset{CH=CH-R^2}{|}}{\overset{COOR^1}{C}}$$

are obtained in a corresponding manner and following the general preparation instructions:

| Example No. | Py | R¹ | R² | X | Physical properties |
|---|---|---|---|---|---|
| 115 | 2-methylpyrimidin-4-yl attached to naphthalen-2-yl | CH₃ | —N(CH₃)₂ | —N(CH₃)— | Mp.: 171–172° C. |
| 116 | 2-methylpyrimidin-4-yl attached to 4-bromophenyl | CH₃ | —N(CH₃)₃ | —N(CH₃)— | |
| 117 | 2-methylpyrimidin-4-yl attached to 3-bromophenyl | CH₃ | —N(CH₃)₂ | —N(CH₃)— | |
| 118 | 2-methylpyrimidin-4-yl attached to benzo[1,3]dioxol-yl | CH₃ | —OCH₃ | —N(CH₃)— | Mp.: 126–127° C. |
| 119 | 2-methylpyrimidin-4-yl attached to pyridin-2-yl | CH₃ | —OCH₃ | —N(CH₃)— | Mp.: 102–104° C. |
| 120 | 2-methylpyrimidin-4-yl attached to 3-methylphenyl | CH₃ | —OCH₃ | —N(CH₃)— | Mp.: 87° C. |

-continued

The following pyrimidyl-substituted acrylic esters of the general formula (I)

(I)

are obtained in a corresponding manner and following the general preparation instructions:

| Example No. | Py | $R^1$ | $R^2$ | X | Physical properties |
|---|---|---|---|---|---|
| 121 | pyrimidine-4-yl attached to phenyl with OCH₃ and Cl substituents | CH₃ | —N(CH₃)₂ | —N(CH₃)— | Mp.: 120–122° C. |
| 122 | pyrimidin-2-yl attached to 3-methylphenyl | CH₃ | —OCH₃ | —N(CH₃)— | |
| 123 | pyrimidin-2-yl attached to biphenyl | CH₃ | —N(CH₃)₂ | —N(CH₃)— | Mp.: 76–77° C. |
| 124 | pyrimidin-2-yl attached to 4-chlorophenyl | CH₃ | —OCH₃ | —N(CH₃)— | Mp.: 121–122° C. |
| 125 | pyrimidin-2-yl attached to phenyl with O-CF₂-CF₂-O fused ring | CH₃ | —OCH₃ | —N(CH₃)— | |

-continued

The following pyrimidyl-substituted acrylic esters of the general formula (I)

are obtained in a corresponding manner and following the general preparation instructions:

| Example No. | Py | R¹ | R² | X | Physical properties |
|---|---|---|---|---|---|
| 126 | 4-methyl-2-(3-methylphenyl)pyrimidine | $CH_3$ | $-N(CH_3)_2$ | $-N(CH_3)-$ | |
| 127 | 4-methyl-2-(4-methoxyphenyl)pyrimidine | $CH_3$ | $-N(CH_3)_3$ | $-N(CH_3)-$ | |
| 128 | 4-methyl-2-(3-bromophenyl)pyrimidine | $CH_3$ | $-OCH_3$ | $-N(CH_3)-$ | Mp.: 111–113° C. |
| 129 | 4-methyl-2-(4-methylphenyl)pyrimidine | $CH_3$ | $-OCH_3$ | $-N(CH_3)-$ | Mp.: 123–124° C. |
| 130 | 4-methyl-2-(4-chlorophenyl)pyrimidine | $CH_3$ | $-N(CH_3)_3$ | $-N(CH_3)-$ | Mp.: 123–124° C. |

-continued

The following pyrimidyl-substituted acrylic esters of the general formula (I)

$$Py-X-\underset{\underset{COOR^1}{|}}{C}=CH-R^2 \qquad (I)$$

are obtained in a corresponding manner and following the general preparation instructions:

| Example No. | Py | R¹ | R² | X | Physical properties |
|---|---|---|---|---|---|
| 131 | (4-methylpyrimidin-2-yl)-phenyl fused with O-CF₂-CF₂-O dioxole | CH₃ | —N(CH₃)₃ | —N(CH₃)— | Mp.: 115–116° C. |
| 132 | 4-methyl-2-(6-chloropyridin-2-yl)pyrimidine | CH₃ | —OCH₃ | —N(CH₃)— | |
| 133 | 4-methyl-2-(3-bromophenyl)pyrimidine | CH₃ | —N(CH₃)₂ | —N(CH₃)— | |
| 134 | 4-methyl-2-(4-methylphenyl)pyrimidine | CH₃ | —N(CH₃)₂ | —N(CH₃)— | Mp.: 145–150° C. |
| 135 | 4-methyl-2-(6-chloropyridin-2-yl)pyrimidine | CH₃ | —N(CH₃)₂ | —N(CH₃)— | |
| 136 | 4-methyl-6-phenyl-2-(3-trifluoromethylphenyl)pyrimidine | CH₃ | —OCH₃ | —N(CH₃)— | |

-continued

The following pyrimidyl-substituted acrylic esters of the general formula (I)

$$Py-X-\underset{\underset{COOR^1}{|}}{C}=CH-R^2 \qquad (I)$$

are obtained in a corresponding manner and following the general preparation instructions:

| Example No. | Py | $R^1$ | $R^2$ | X | Physical properties |
|---|---|---|---|---|---|
| 137 |  (4-chlorophenyl pyrimidinyl) | $CH_3$ | $-O-CH_2-C_6H_5$ | $-N(CH_3)-$ | Mp.: 119–122° C. |
| 138 | (3,4-dichlorophenyl pyrimidinyl) | $CH_3$ | $-OC_2H_5)_2$ | $-N(CH_3)-$ | Mp.: 163–165° C. |
| 139 | (4-methoxyphenyl pyrimidinyl) | $CH_3$ | $-OCH_3$ | $-N(CH_3)-$ | |

*The $^1H$ NMR-spectra were recorded in deuterochloroform (CDCl$_3$) with tetramethylsilane (TMS) as the internal standard. The data given are the chemical shift as δ value in ppm.

USE EXAMPLES

In the use examples which follow, the compounds listed below were employed as comparison substances:

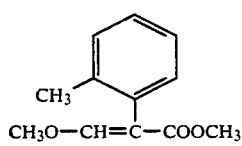

(A)

Methyl 3-methoxy-2-(2-methylphenyl)-acrylate (disclosed in EP 178,826)

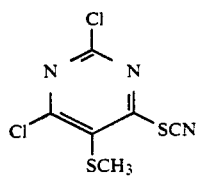

(B)

2,4-Dichloro-5-methylthiopyrimidinyl 6-thiocyanate (disclosed in U.S. Pat. No. 4,652,569).

EXAMPLE A

Erysiphe test (barley)/protective

Solvent: 100 parts by weight of dimethyl formamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds of the following preparation examples: 16, 45, 49, 50 and 51.

Comparison compound (B) is ineffective.

EXAMPLE B

*Leptosphaeria nodorum* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain in a incubation cabin for 48 hours at 20° C. and a relative atmospheric humidity of 100%.

The plants are placed in a greenhouse at a temperature of about 15° C. and a relative atmospheric humidity of about 80%.

Evaluation is carried out 10 days after the inoculation.

In this test, an effectiveness which is up to 70 degrees of action (measured in %) better in comparison with the known compound (A) is shown, for example, by the compounds of the following preparation examples: 16 and 17.

EXAMPLE C

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain for 48 hours in an incubation cabin at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds of the following preparation examples: 16, 17 and 49.

EXAMPLE D

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds of the following preparation examples 1, 45, 46, 47, 49, 50, 51 and 73.

EXAMPLE E

Plasmopara test (vines)/protective
Solvent: 4 7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20 to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compounds of the following preparation examples: 45, 50, 51, 65, 66, 73, 87, 89 and 90.

We claim:

1. Pyrimidyl-substituted acrylic esters of the formula (I)

in which
R$^1$ represents a straight-chain or branched alkyl having 1 to 6 carbon atoms,
R$^2$ represents dialkylamino having in each case 1 to 6 carbon atoms in the individual alkyl moieties, or represents a radical —O—R$^3$,
X represents oxygen, sulphur, or a radical

and
Py represents 2-pyrimidyl, 4-pyrimidyl or 5-pyrimidyl, each of which is monosubstituted or polysubstituted by identical or different substituents, suitable substituents in each case being:
halogen, cyano, nitro, in each case straight-chain or branched alkyl, alkoxy or alkylthio, each of which has 1 to 9 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl, alkoximinoalkyl, dialkylamino or dialkylaminocarbonyl, each of which has 1 to 4 carbon atoms in the individual alkyl moieties, in each case straight-chain or branched alkenyl or alkinyl, each of which has 2 to 8 carbon atoms, cycloalkyl or cycloalkenyl, each of which has 3 to 7 carbon atoms and each of which is optionally monosubstituted or polysubstituted by $C_1$-$C_4$-alkyl, or represents double-linked alkanediyl having 3 to 5 carbon atoms, or represents aryl, aryloxy, arylthio, arylamino, N-alkyl-arylamino, arylcarbonyl, aralkyl, arylalkenyl, arylalkinyl, arylalkyloxy, arylalkylthio, each of which has 6 or 10 carbon atoms in the aryl moiety and, if appropriate, 2 to 6 carbon atoms in the straight-chain or branched alkyl moiety or, if appropriate, 2 to 6 carbon atoms in the straight-chain or branched alkenyl or alkinyl moiety, and each of which is optionally monosubstituted or polysubstituted in the aryl moiety by identical or different substituents selected from the group consisting of halogen, alkyl, cycloalkyl, alkoxy, alkylthio, halogenoalkyl, halogenoalkoxy, halogenoalkylthio, formyl, dioxyalkylene, halogen-substituted dioxyalkylene, or in each case optionally substituted phenyl, phenoxy, benzyl, phenylethyl, phenylethenyl or phenylethinyl, or heteroaryl, heteroaryloxy, heteroarylthio, heteroarylamino, N-alkyl-heteroarylamino, heteroarylcarbonyl, heteroarylalkyl, heteroarylalkenyl, heteroarylalkinyl, heteroarylalkyloxy or heteroarylalkylthio, wherein the heteroaryl moiety is in each case selected from the group consisting of pyridyl, pyrimidyl, pyrazolyl, oxazolyl, thiazolyl, thienyl, furyl, thiadiazolyl, oxadiazolyl, imidazolyl or triazolyl, each of which is optionally monosubstituted or polysubstituted by identical substituents selected from the group consisting of halogen, alkyl, cycloalkyl, alkoxy, alkylthio, halogenoalkyl, halogenoalkoxy, halogenoalkylthio, formyl, dioxyalkylene, halogen-substituted dioxyalkylene, or in each case optionally substituted phenyl, phenoxy, benzyl, phenylethyl, phenylethenyl or phenylethinyl and wherein, if appropriate, the straight-chain or branched alkyl moiety has 1 to 6 carbon atoms and, if appropriate, the straight-chain or branched alkenyl or alkinyl moiety has 2 to 6 carbon atoms; where $R^3$ represents a straight-chain or branched alkyl having 1 to 6 carbon atoms or aralkyl having 1 to 4 carbon atoms in the straight-chain or branched alkyl moiety and 6 or 10 carbon atoms in the aryl moiety, and $R^4$ represents hydrogen, straight-chain or branched alkyl having 1 to 6 carbon atoms, or represents aralkyl or aryl each of which has 1 to 6 carbon atoms in the straight-chain or branched alkyl moiety and 6 or 10 carbon atoms in the particular aryl moiety, each of which is optionally monosubstituted or polysubstituted in the aryl moiety by identical or different substituents, suitable substituents in the aryl moiety in each case being those mentioned in the case of Py.

2. Pyrimidyl-substituted acrylic esters of the formula (I) according to claim 1, in which $R^1$ represents methyl, ethyl, n- or i-propyl, or n-, i-, s- or t-butyl, $R^2$ represents dialkylamino having in each case 1 to 4 carbon atoms in the individual alkyl moieties, or represents a radical —O—$R^3$, X represents sulphur or a radical

and

Py represents 2-pyrimidyl or 4-pyrimidyl, each of which is monosubstituted to trisubstituted by identical or different substituents, where at least one substituent represents phenyl, naphthyl, phenoxy, phenylthio, N-methyl-phenylamino, phenylcarbonyl, benzyl, phenylethyl, phenylpropyl, phenylethenyl, phenylethinyl, benzyloxy, cyclohexenyl or heteroaryl, each of which is optionally monosubstituted to trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy, formyl, trifluoromethylthio, dioxymethylene, dioxyethylene, tetrafluorodioxyethylene, difluorodioxymethylene, cyclopentyl, cyclohexyl, or comprising phenyl, phenoxy, benzyl, phenylethyl, phenylethenyl or phenylethinyl, each of which is optionally monosubstituted to trisubstituted by identical or different substituents by fluorine, chlorine, methyl, methoxy or trifluoromethyl- in addition, the pyrimidyl is optionally substituted by fluorine, chlorine, bromine, cyano, nitro, methyl, ethyl, n- or i-propyl, n-, i-, s- or t-butyl methoxy, ethoxy, n- or i-propoxy, methylthio, trifluoromethyl, trifluoromethoxy, trichloromethoxy, trifluoromethylthio, methoxycarbonyl, ethoxycarbonyl, methoximinomethyl, ethoximinomethyl, methoximinoethyl, ethoximinoethyl, dimethylamino, diethylamino, dimethylcarbamoyl, diethylcarbamoyl, allyl, butenyl, ethinyl, vinyl, propargyl, cyclopentyl, cyclohexyl, 1,3-propanediyl or 1,4-butanediyl; where $R^3$ represents methyl, ethyl, n- or i-propyl, n-, i-, s- or t-butyl or benzyl and $R^4$ represents hydrogen, methyl, ethyl, n- or i-propyl, n-, i-, s- or t-butyl, or benzyl or phenyl.

3. Pyrimidyl-substituted acrylic esters of the formula (I) according to claim 1, in which $R^1$ represents methyl or ethyl, $R^2$ represents methoxy or ethoxy, X represents a radical

and

Py represents 2-pyrimidyl or 4-pyrimidyl, each of which is monosubstituted to trisubstituted by identical or different substituents, where at least one substituent in each case represents phenyl, naphthyl, phenoxy, cyclohexenyl, cyclohexyl, benzyl, pyridyl, pyrimidyl, pyrazolyl, oxazolyl, thiazolyl, thienyl, furyl, thiadiazolyl, oxadiazolyl, imidazolyl or triazolyl, each of which is optionally benzo-fused and/or monosubstituted to trisubstituted by identical or different substituents from the series comprising fluorine, chlorine, bromine, methyl, ethyl, t-butyl, methoxy, ethoxy, trifluoromethyl, trifluoromethoxy, dioxymethylene, difluorodioxymethylene dioxyethylene, tetrafluorodioxyethylene, phenylethenyl, phenylethinyl, benzyl, cyclohexyl, phenoxy, methoxyphenyl, formyl or phenyl, and the pyrimidyl is optionally substituted by chlorine, bromine, cyano, nitro, methyl, ethyl, methoxy, ethoxy, methylthio, trifluoromethyl, trichloromethyl, trifluoromethoxy, trifluoromethylthio, methoxycarbonyl, ethoxycarbonyl, dimethylamino, cyclopentyl, cyclohexyl, 1,3-propanediyl or 1,4-butandiyl, and where $R^4$ represents methyl, ethyl or benzyl.

4. 3-Hydroxyacrylic esters of the formula (IV)

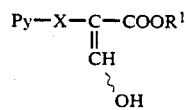

in which

Py, X and $R^1$ have the meaning given in claim 1.

5. A fungicidal composition comprising a fungicidally effective amount of a pyrimidyl-substituted acrylic ester according to claim 1 and an extender.

6. A method of combating fungi comprising applying to the fungi or their habitat a fungicidally effective amount of a pyrimidyl-substituted acrylic ester according to claim 1.

* * * * *

UNITED STATES PATENT AND TRADEMARK OFFICE
CERTIFICATE OF CORRECTION

PATENT NO. : 5,231,097
DATED : July 27, 1993
INVENTOR(S) : Klausener, et al.

It is certified that error appears in the above-indentified patent and that said Letters Patent is hereby corrected as shown below:

| | |
|---|---|
| Col. 68, line 4 | After " X represents " insert -- oxygen ,-- |
| Col. 68, lines 40-41 | Delete " ethoximimonethyl " and substitute --- ethoximinoethyl -- |
| Col. 69, line 10 | After " substituted by " insert -- fluorine ,-- |

Signed and Sealed this

Fourth Day of April, 1995

Attest:

BRUCE LEHMAN

*Attesting Officer*     *Commissioner of Patents and Trademarks*